(12) United States Patent
Hernández Miramontes et al.

(10) Patent No.: US 10,688,068 B2
(45) Date of Patent: *Jun. 23, 2020

(54) MIXTURE OF CARBOXYLIC ACIDS FOR TREATING PATIENTS WITH KIDNEY FAILURE

(71) Applicant: Jorge Antonio Hernández Miramontes, Jalisco (MX)

(72) Inventors: Jorge Antonio Hernández Miramontes, Jalisco (MX); Jorge Alberto Hernández Villanueva, Jalisco (MX)

(73) Assignee: Jorge Antonio Hernández Miramontes, Jalisco (MX)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,620

(22) PCT Filed: Nov. 4, 2015

(86) PCT No.: PCT/MX2015/000144
§ 371 (c)(1),
(2) Date: Jul. 31, 2017

(87) PCT Pub. No.: WO2016/153331
PCT Pub. Date: Sep. 29, 2016

(65) Prior Publication Data
US 2018/0000764 A1 Jan. 4, 2018

(30) Foreign Application Priority Data
Mar. 20, 2015 (MX) .......................... A/2015/003641

(51) Int. Cl.
| | | |
|---|---|---|
| *A61K 31/194* | (2006.01) | |
| *A61K 33/00* | (2006.01) | |
| *A61K 31/714* | (2006.01) | |
| *A61K 31/675* | (2006.01) | |
| *A61K 31/593* | (2006.01) | |
| *A61K 31/525* | (2006.01) | |
| *A61K 31/519* | (2006.01) | |
| *A61K 31/51* | (2006.01) | |
| *A61K 31/455* | (2006.01) | |
| *A61K 31/4188* | (2006.01) | |
| *A61K 31/375* | (2006.01) | |
| *A61K 31/205* | (2006.01) | |

(Continued)

(52) U.S. Cl.
CPC ............ *A61K 31/194* (2013.01); *A23L 33/10* (2016.08); *A23L 33/15* (2016.08); *A23L 33/16* (2016.08); *A61K 9/0014* (2013.01); *A61K 9/0053* (2013.01); *A61K 31/185* (2013.01); *A61K 31/19* (2013.01); *A61K 31/197* (2013.01); *A61K 31/205* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/714* (2013.01); *A61K 33/00* (2013.01); *A61K 33/06* (2013.01); *A61K 33/10* (2013.01); *A61K 33/26* (2013.01); *A61K 45/06* (2013.01); *C07C 55/10* (2013.01); *C07C 55/20* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,500,232 A | * | 3/1996 | Keating ................... | A23L 2/68 426/590 |
| 6,376,544 B2 | * | 4/2002 | Lowry ................... | A23L 33/10 514/565 |

(Continued)

FOREIGN PATENT DOCUMENTS

| | | |
|---|---|---|
| EP | 0938849 A1 | 9/1999 |
| WO | 2010130028 A1 | 11/2010 |
| WO | 2014035246 A1 | 3/2014 |

OTHER PUBLICATIONS

Cianciaruso et al. Effect of a Low- Versus Moderate-Protein Diet on Progression of CKD: Follow-up of a Randomized Controlled TrialAmerican Journal of Kidney Diseases, vol. 54, No. 6 Dec. 2009: pp. 1052-1061 (Year: 2009).*

(Continued)

*Primary Examiner* — Michael P Cohen
(74) *Attorney, Agent, or Firm* — Maier & Maier, PLLC

(57) ABSTRACT

Our invention is a mixture of carboxylic acids: citric acid, succinic acid, fumaric acid and malic acid, and any possible combinations thereof. This product is used orally or also intravenously, in the treatment of patients with chronic renal failure, hyperammonemia or human conditions having negative nitrogen balance. This product is beneficial in decreasing the serum values of urea and serum ammonium, while promoting by transamination of the oxalacetate formed via succinate, fumarate and malate, the biosynthesis of non-essential amino acids; by transamination of the alpha ketoglutarate formed via citrate, it generates glutamic acid and related amino acids such as glutamine. This treatment prevents, preserves and even improves kidney function. In other patients it delays deterioration of renal function and the urgent need for renal replacement therapy. In others, it is used as a supplemental renal replacement treatment to improve the patient's quality of life and improve laboratory parameters.

6 Claims, 3 Drawing Sheets

(51) Int. Cl.
  *A61K 31/197* (2006.01)
  *A61K 31/19* (2006.01)
  *A61K 9/00* (2006.01)
  *A61K 33/10* (2006.01)
  *A61K 33/26* (2006.01)
  *A23L 33/10* (2016.01)
  *A23L 33/15* (2016.01)
  *A23L 33/16* (2016.01)
  *C07C 55/20* (2006.01)
  *C07C 55/10* (2006.01)
  *A61K 33/06* (2006.01)
  *A61K 45/06* (2006.01)
  *A61K 31/185* (2006.01)

(56) References Cited

U.S. PATENT DOCUMENTS

| | | | | |
|---|---|---|---|---|
| 6,488,961 B1* | 12/2002 | Robinson | ............ | A61K 9/0007 424/43 |
| 7,052,725 B2* | 5/2006 | Chang | ................ | A23L 2/385 426/548 |
| 2003/0211204 A1* | 11/2003 | Fields | ................ | A23L 2/02 426/74 |
| 2008/0226799 A1* | 9/2008 | Lee | ............ | A23L 2/56 426/590 |
| 2009/0186127 A1* | 7/2009 | Krumhar | ................ | A23L 2/52 426/72 |
| 2010/0003384 A1* | 1/2010 | Iacovone | ................ | A23L 2/40 426/285 |
| 2011/0207822 A1 | 8/2011 | Lopes | | |

OTHER PUBLICATIONS

Web page from National Kidney Foundation, "Fluid Overload in a Dialysis Patient", downloaded from https://www.kidney.org/atoz/content/fluid-overload-dialysis-patient on Sep. 1, 2019. (Year: 2019).*
International Search Report dated May 4, 2016 in corresponding Application No. PCT/MX2015/000144; 3 pgs.
International Preliminary Report on Patentability dated Nov. 21, 2016 in corresponding Application No. PCT/MX2015/000144; 5 pgs.

* cited by examiner

Figure 1. Citric acid cycle (Krebs cycle)
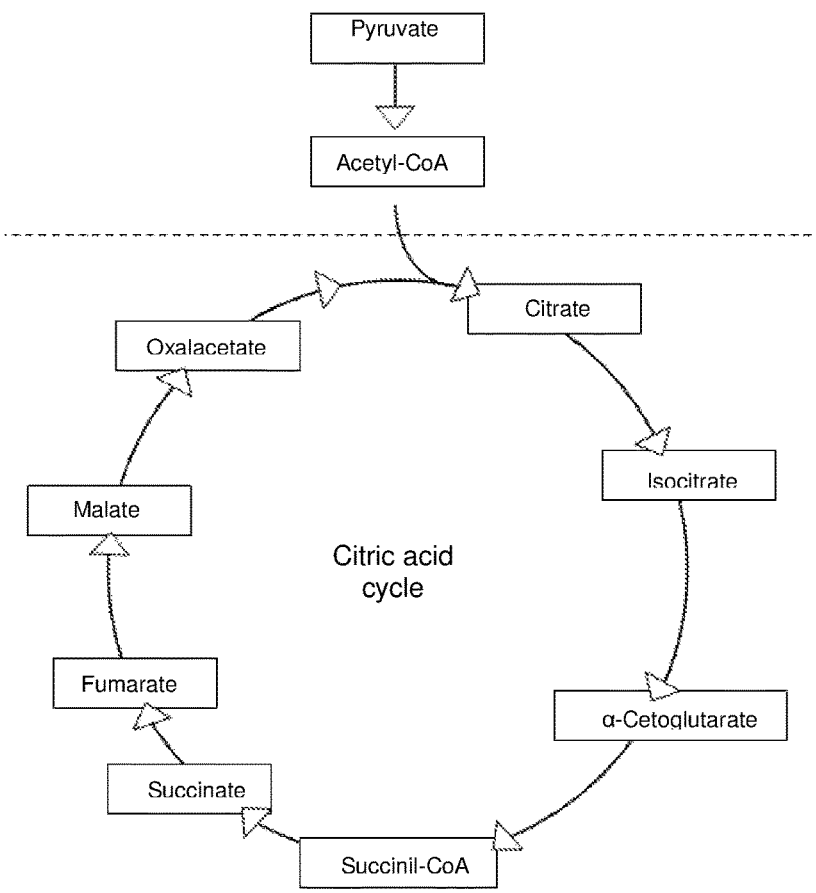

Figure 2. Anaplerotic pathways for replacement of Krebs cycle intermediates.
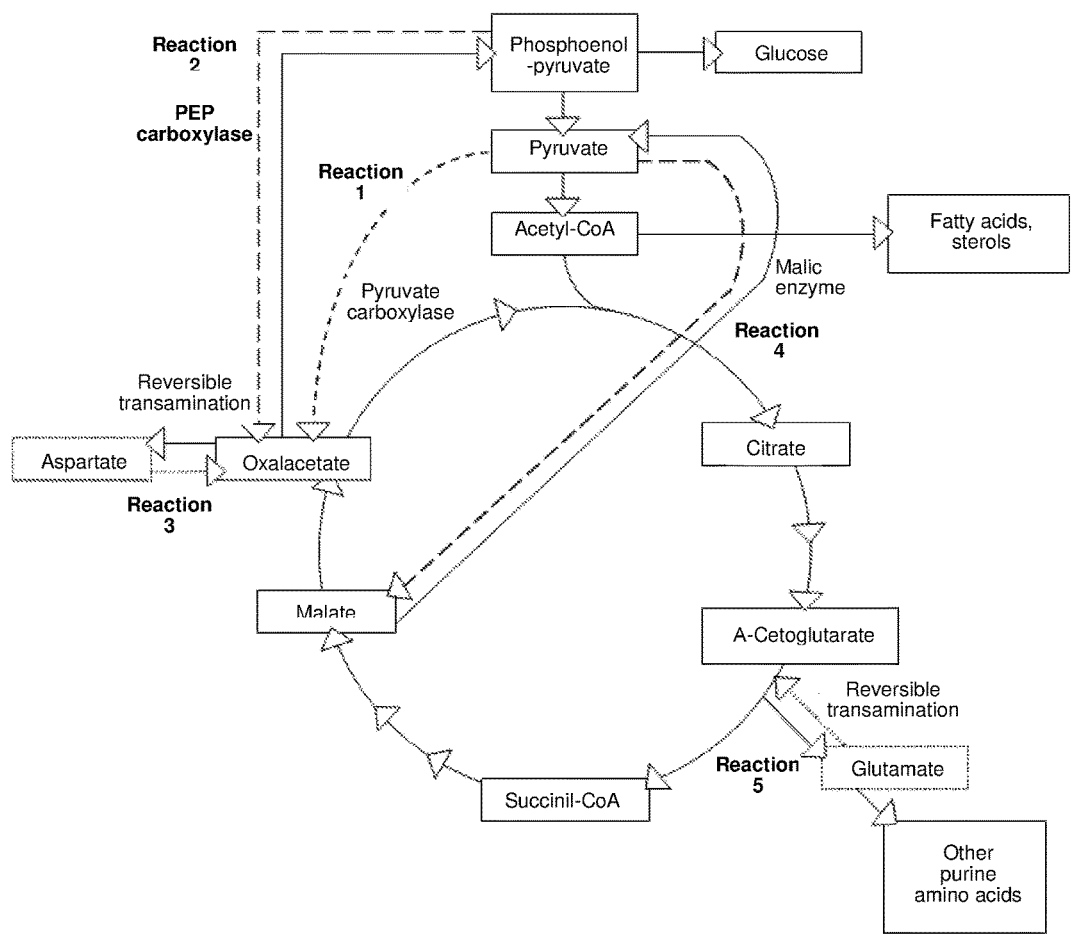

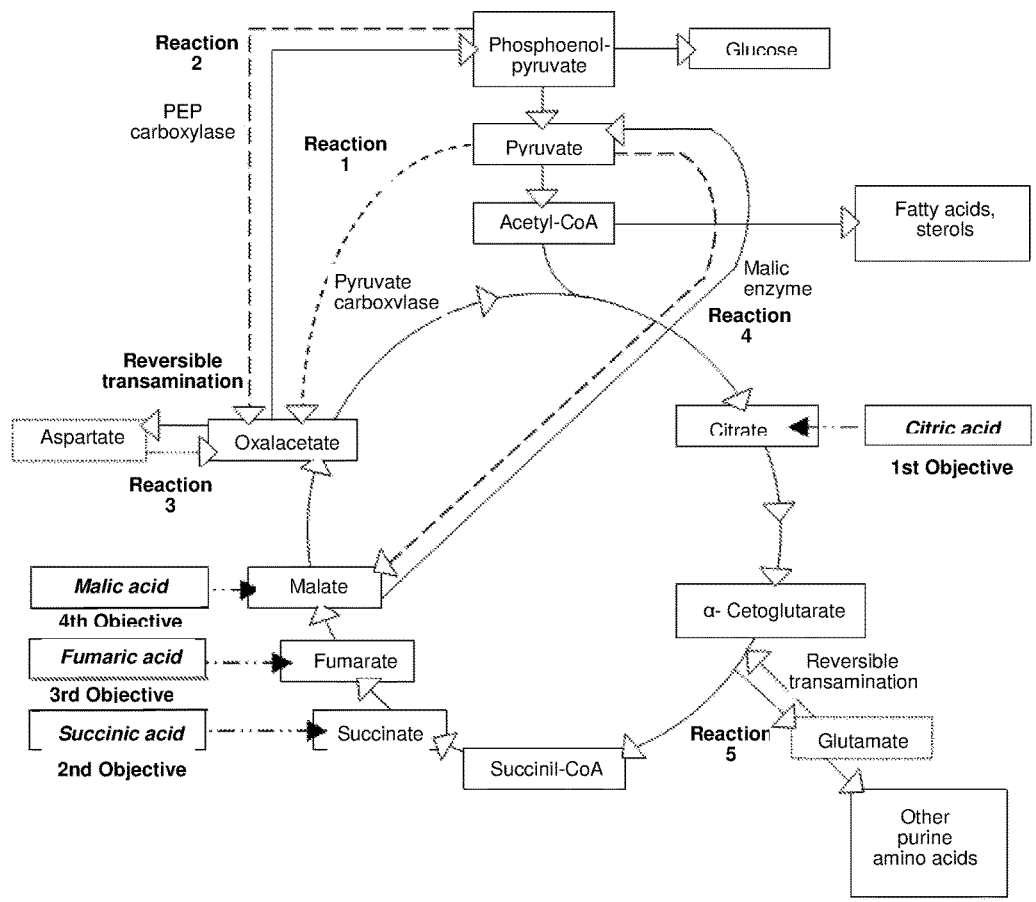
Figure 3. External replacement of intermediates of the citric acid cycle.

MIXTURE OF CARBOXYLIC ACIDS FOR TREATING PATIENTS WITH KIDNEY FAILURE

II.1. Chronic renal failure
II.2. Acute renal failure
II.3. Chronic or acute hepatopathy occurring with hyperammonemia
II.4. Congenital diseases with enzymatic alterations of the urea cycle
II.5. Pathological human conditions having negative nitrogen balance, namely:
II.5.1. Sepsis
II.5.2. Burns
II.5.3. Postoperative
II.5.4. Complement of parenteral nutrition entailing mixture of amino acids
II.5.5. Enteral nutrition supplement
II.5.6. Sarcopenia
II.5.7. Cancer
II.5.8. Malnutrition
II.6. Diabetes Mellitus With regard to Chronic Kidney Disease (CKD), there has been a dramatic increase in both the prevalence and incidence of this disease in practically the whole world. The last stage of this group of chronic kidney diseases is the End-Stage Renal Disease (ESRD). Figures such as the following show the panorama: a recent study in Mexico in 2010 entitled Epidemiology of Chronic Renal Failure in Mexico estimated an incidence of 377 new cases per million inhabitants and a prevalence of 1142 cases per million inhabitants, as well as about 52,000 patients in renal replacement therapy to that date. In the United States of America, according to the 2010 and 2011 Annual Data Report, one out of ten American adults has some degree of CKD. The incidence of CKD increases substantially in people over 65 years or older. The incidence in this age group doubled from 2000 to 2008. As for the incidence of ESRD in that country, it was estimated at a little more than 360 new cases per million inhabitants; with regard to the prevalence at the end of 2009, 871,000 patients received renal replacement therapy. Between 1980 and 2009, the prevalence of ESRD increased by 600% with a prevalence of 1,738 patients per million inhabitants. Regarding CKD stages one to five, it is estimated that in Mexico 8.5% of the Mexican population has some degree of CKD, defined as a reduction of the glomerular filtration rate lower than 60 ml/min/1.73 m² of body surface. Meanwhile, a report by Sarah L. White et al. from the World Health Organization reports that more than 1.4 million people in the world are in some type of renal replacement therapy, 80% of which is provided in developed countries.

Currently, the most frequent causes of ESRD are: Non-insulin dependent diabetes mellitus as the first cause, Systemic Arterial Hypertension as the second, and miscellaneous glomerulopathies as the third cause. The first two pathologies (DM II and SAH), combined with a longer life expectancy of the world population, augur an unfavorable panorama regarding the CKD and its final stage, the ESRD, so the current figures show an upward trend.

This ESRD is accompanied by: 1) extremely high treatment costs, 2) high morbidity, 3) increased mortality, and 4) greatly reduced quality of life.

With regard to item (1), extremely high treatment costs, ESRD is considered a catastrophic disease, since it can mean ruin for most families and a significant economic burden for national health systems. In the United States of America, according to the 2009 Annual Report Data System, the cost for a hemodialysis patient was $80,000 dollars annually, $60,000 dollars for peritoneal dialysis patients and $30,000 dollars per year for renal transplant patients. In other countries with available information, the annual costs per patient are: $7,332 USD in Brazil, $7,500 USD in China, $5,000 USD in India and $6,240 USD in Indonesia (White, Chadban, Jan, Chapman, & Cass, 2008). In Mexico, the costs of hemodialysis and continuous ambulatory peritoneal dialysis were estimated at $21,861 USD and $8,489 USD respectively (Schettino Maimone, et al., 1997).

In order to stop the alarming growth of the ESRD "epidemic" and, consequently, reduce the costs of its treatment, the current trend worldwide is towards prevention of CKD; however, considering that the pathologies leading to CKD and finally to its last stage, ESRD, are DM II and SAH, and since these two pathologies are becoming more frequent in the general population, the picture for the future is gloomy. Such is the situation that widely recognized international organizations such as the National Kidney Foundation (NKF), the International Society of Nephrology (ISN) and the World Health Organization (WHO) endorsed the launching of the first World Kidney Day in March 2006.

Regarding morbidity, despite medical and technical advances, patients with end-stage renal disease treated with dialysis often continue to have problems. Constitutional symptoms such as fatigue and weakness persist even with adequate correction of anemia with erythropoietin. Progressive cardiovascular disease, autonomic and peripheral neuropathy, bone disease and sexual dysfunction are common even in patients who may be adequately treated with dialysis, which is not surprising since even the most efficient dialysis regimens contribute only 10 to 20% of the removal of low molecular weight solutes such as urea. Removal of solutes of higher molecular weight is still less efficient than in normal conditions two kidneys with 1 million nephrons each functioning at 100% would perform. In addition, dialysis patients may become dependent on their families or caregivers in terms of physical, emotional and financial assistance.

In regard to mortality, the United States Renal Data System (USRDS) shows the following figures in its 2009 report according to statistics from the United States of America:

1.—The average life expectancy of the American citizen over 55 years of age is 26 years, that is 81 years.
2.—The average life expectancy of the American citizen over 55 years of age who receives a kidney transplant from a living individual is 15 years, that is 70 years; but,
3.—The average life expectancy of a patient over 55 years of age on dialysis treatment is only 5 years, i.e., 60 years.
4.—The overall life expectancy of all patients in the United States who undergo dialysis treatment is 3 years. This information, in the shortened global life expectancy, is a consequence of the fact that in patients who start dialysis treatment the average life at the beginning of the dialysis treatment is greater than 65 years. These results of hemodialysis treatment (because in the United States 90% of patients receive hemodialysis versus peritoneal dialysis in only about 10%) have not changed substantially over the past 20 years.

In Mexico, according to the study dated February 2010, the average survival for the two modalities of peritoneal dialysis was 30.6 months and 32 months for patients on hemodialysis.

III. STATE OF THE ART

Until now, the treatment of patients with Stage V chronic kidney disease, also known as End-Stage Renal Disease, defined as a glomerular filtration rate of less than 15 milliliters/minute/1.73 m² of body surface area, has consisted of:
1. Substitute or Replacement Renal Treatment, which consists of three options with modalities, in turn, in each one of them:
1.a. Hemodialysis is a treatment entailing high costs reported in the United States of about $80,000 USD annually. In Mexico an overall life expectancy of 32 months is estimated according to the study "Epidemiology of Chronic Renal Disease in Mexico." On the other hand, in the United States of America an average global life expectancy of around 36 months is reported. With regard to quality of life, it is necessary to mention that patients, in most cases, except for those in which hemodialysis is performed at home, should go to a specialized hospital or clinic three times a week, remaining 3 to 4 hours in the dialysis session.
1.b. Peritoneal Dialysis, with a reported cost in the United States of America of about $60,000 per year and a similar life-time to hemodialysis in that country. In Mexico there was an overall average life expectancy of 30.6 months (Méndez-Duran, Méndez-Bueno, Tapia-Yáñez, Muñoz Montes, & Aguilar-Sánchez, 2010). It is necessary to mention that its main complication is the generally bacterial peritonitis with an incidence rate of one event per patient per year and, if severe, a recovery time of 28 days (Ministry of Health, 2009).
1.c. Kidney transplantation with two modalities, namely, cadaveric donor with a survival similar to that of patients in the peritoneal dialysis or hemodialysis programs, or living donor with an average life expectancy of 15 to 17 years; as well as a great improvement in the quality of life and an important decrease in the annual costs of treatment that in the United States of America were estimated at around 30,000 dollars per year.

In addition to renal replacement therapy, either with a) hemodialysis, b) peritoneal dialysis, or c) renal transplantation, in a complementary, adjuvant, adjunctive manner, but not supplementary, or as replacement of said renal replacement therapies, adjuvant treatments are provided, consisting of:
2. Phosphorus chelating treatments—since patients with ESRD have hyperphosphatemia—it is necessary to add phosphorus chelating drugs to patients with hyperphosphatemia immediately after meals to chelate and fix phosphorus in food. These drugs include: 1) aluminum hydroxide, currently in disuse because of its proven toxicity, resulting in encephalopathy and osteomalacia. Another therapy consists of calcium salts, 2) calcium acetate or 3) calcium carbonate, which also chelate phosphorus; another, 4) lanthanum carbonate and recently a phosphorus chelator consisting of a copolymer known as 5) sevelamer.
3. Adjuvant treatment for anemia of renal failure, which in most patients is secondary to a deficiency of renal production of erythropoietin. Treatment with recombinant erythropoietins manufactured by biotechnology, such as 1) erythropoietin alfa, 2) erythropoietin beta, and 3) erythropoietins with a higher degree of glycosylation and longer shelf life such as epoetin, 4) darbepoetin and 5) CERA.
4. Treatment with calcitriol, the active form of vitamin D, since the insufficient kidney has a marked decrease in the conversion of inactive vitamin D to the activated form 1, 25 dihydroxy cholecalciferol, which is involved in the intestinal absorption of calcium.
5. Prevention and treatment of hyperkalemia mainly by: 1) avoiding consumption of foods rich in potassium and 2) avoiding and correcting metabolic acidosis, a condition that aggravates hyperkalemia, and ultimately, when hyperkalemia is severe, medicines are used to lower serum potassium such as: 3) polarizing solutions consisting of glucose solutions and insulin that divert extracellular potassium to the intracellular compartment, 4) beta-adrenergic drugs such as salbutamol, 5) loop diuretics such as furosemide that removes potassium via the kidney, and 6) sodium potassium exchange resins such as kayexalate (sodium polystyrene sulfonate) that decrease the intestinal absorption of potassium.
6. Treatment and prevention of hypo calcemia with supplements of calcium salts such as: 1) calcium acetate, 2) calcium carbonate, 3) calcium gluconate, 4) coral calcium and/or 5) oseinic calcium.
7. Treatment of fluid overload, if any, with fluid restriction and use of diuretics, especially loop.
8. Treatment of hyperuricemia, if any, with allopurinol.
9. Treatment of co-morbid conditions such as treatment of diabetes mellitus, treatment of hypertension, treatment of glomerulopathies or diseases that caused chronic kidney disease, treatment of pre-existing cardiovascular disease, treatment of malnutrition, if any, which is very common, and other conditions such as hypercholesterolemia and/or hypertriglyceridemia.
10. Treatment with sulodexide in patients with diabetic nephropathy. European patent EP-0624374-B1, entitled "Use of Sulodexide and Medicaments Containing It for the Treatment of Diabetic Nephropathy," a complication that may result in ESRD, proposes the use of such a molecule, belonging to the group of glucosaminoglycans of natural origin and extracted from the intestinal mucosa of mammals, in the therapeutic arsenal to treat CKD and its final stage, ESRD. This patent states that sulodexide "causes a significant and significant decrease in urinary albumin excretion."
11. Treatment with sulphated polysaccharides combined with L-amino acids, as described in the Chinese patent CN-1285340-C, which exerts an improvement in renal function indexes and serum albumin levels.
12. Supplementary and adjuvant food treatment consisting of mixtures of keto analogs of essential branched chain amino acids such as valine keto-analogue, leucine keto-analogue, isoleucine keto-analogue and methionine hydroxyalkane. These in combination with different essential L-amino acids constitute a suggested treatment for patients in stage 5 and 4 renal disease. In the pre-dialytic stage, corresponding to stages 4 and 3 of chronic kidney disease with glomerular filtration rates of 15 to 29 and 30 to 59 ml./min/1.73 m² of body surface respectively, an adjusted hypo protein diet of 0.6 to 0.8 grams of protein per kilo of weight per day is prescribed, preferably proteins of high biological quality because of their higher content of essential amino acids (tryptophan, histidine, arginine, lysine, methionine, valine, leucine, isoleucine, phenylalanine, threonine) primarily whey protein and egg white protein. The above in order to reduce as much as possible a greater intake than the necessary proteins which, ingested in excess or, very important, in poor biological quality because of its low content of essential amino acids, would be subject to catabolic metabolism, which, as a consequence of the deamination of 19 alpha-L-amino acids, would generate high amounts of ammonium, which in subsequent metabolic steps, specifically through the urease cycle or Krebs-Henseleit, mainly performed in the liver at the level of the hepatocyte cytosol, generates urea as the end product of this cycle. Urea, also known as carbamide, subsequently returns to the general circulation and is eliminated from our body mainly via the kidney. A small fraction, up to 10% of urea, is removed with sweat, and about a quarter of the circulating urea in blood passes into the intestine where, by action of the urease of ureolytic bacteria residing in the intestine, it is converted again to ammonium and carbon dioxide, said ammonium being absorbed to the portal circulation and its passage to the liver.

It is in this modality of coadjuvant and complementary dietary treatment of chronic renal disease (point number 12 of our presentation) in which patients who develop end-stage renal disease receive a treatment consisting of renal replacement therapy: peritoneal dialysis, hemodialysis or renal transplantation. In addition, they are given a treatment for co-morbid conditions and alterations characteristic of chronic renal failure. In addition to the aforementioned measures and treatments, a hypo-protein and hypercaloric diet is prescribed, which typically ranges from 0.6 to 0.8 grams of protein per kilo of weight per day, in order to avoid an excess of protein intake which would consequently cause an excessive intake of the amino acids that are part of it. Finally this excess of amino acids would lead to a catabolism thereof, since human beings, unlike the handling of carbohydrates, fatty acids and glycerol contained in nutrients, do not have polymeric macromolecules for storage, as is the case of glucose that by glycogenesis is stored as glycogen in liver and muscle; or oils and fats from food stored in the form of triacylglycerols in the adipocytes of fat tissue—which is not the case of amino acids. Amino acids that are not used in anabolism, after amino group deamination, their carbon skeletons enter catabolic pathways to generate energy. Then, the amino group (NH2) generates ammonia (NH3) formation that immediately in the aqueous medium of the organism is converted to ammonium (NH4), which in the next metabolic step enters the urea cycle, where it becomes urea to be eliminated through the kidney mainly.

In order to be able to influence and intervene at this stage, i.e., to avoid excessive or unnecessary and undesirable ammonium formation, the medical community has long sought, designed and used treatment modalities that, on the one hand, reduce protein intake, but at the same time maintain a positive nitrogen balance and an energy balance to avoid the excessive formation of nitrogenous waste products. In this regard, the U.S. Pat. No. 2,457,820-A proposed a mixture of essential amino acids administered parenterally, rectally or orally to maintain an appropriate nitrogen balance in those medical conditions where there is an excessive loss of proteins, for example, after injury, post-operative trauma, severe malnutrition, gastrointestinal tract damage and the like (Howe & Max, 1949). U.S. Pat. No. 3,764,703-A consists of a mixture of eight essential amino acids optionally combined with L-arginine or L histidine for use in patients with chronic kidney disease where the mixture for intravenous administration contains 2.5 to 15 grams of nitrogen per liter of solution (Bergstrom, et al., 1973). Said mixture is also present in tablets for oral administration. Basically these two prior patents involve the use of a mixture of essential amino acids. Subsequently, U.S. Pat. No. 4,100,161-A "Promotion of Protein Synthesis and Suppression of Urea Formation in the Body by Keto Analogs of Essential Amino Acids" discloses a process for preparing a composition for food treatment by patenting a mixture of mixed salts formed between alpha-keto analogs of branched-chain amino acids, specifically keto analogs of valine, leucine and isoleucine, these three of the essential amino acid series, combined with basic alpha-L-amino acids of ornithine, lysine or histidine. In addition, essential amino acids, specifically L-tyrosine, L-threonine, as well as calcium alpha hydroxy-gamma-methylthiobutyrate are added to the described mixture (Walser, Promotion of Protein Synthesis and Suppression of Urea Formation in the Body by Keto Analogs of Essential Amino Acids, 1978). With regard to essential L-amino acids, the amounts in the mixture are so small that they can be ingested by selecting proteins of high biological quality such as whey isolated protein or egg white. It is also extremely important to mention that in its composition said patent describes the use of racemic mixtures (i.e., L-isomers and D-isomers) of alpha keto analogs of branched chain amino acids, and is very well known scientifically that the constituent amino acids of proteins of man, all 19 amino acids, are of the L series, except glycine which, not containing a chiral carbon, lacks isomers thereof, so that, strictly speaking, only 25% of said composition, L-keto analogs of amino acids valine, leucine and isoleucine are extremely useful and effectively capture the serum ammonium to be transformed into the corresponding amino acids valine, leucine and isoleucine. Walser's U.S. Pat. No. 4,100,293-A consists of the use of alpha keto analogs of valine, leucine, isoleucine, phenylalanine, methionine and L histidine. In addition, the mixture may contain L-arginine, L-lysine, L-threonine and L-tryptophan for the treatment of hepatic diseases with hyperammonemia or portosystemic encephalopathy, as well as for the treatment of children with congenital hyperammonemia due to alterations in the enzymes of the urea cycle or Krebs-Henseleit. Walser's U.S. Pat. No. 4,228,099-A describes the use of ornithine and arginine salts, combined with salts of keto analogs of branched-chain amino acids, valine, leucine and isoleucine, in the treatment of patients with liver diseases who are suffering from hyperammonemia and portosystemic encephalopathy. The use of these compounds in the treatment of patients with renal insufficiency is also useful. Walser's U.S. Pat. No. 4,296,127-A consists of mixed salts of semi-essential and essential amino acids. Semi-essential amino acids are selected from ornithine, arginine, cysteine, cystine and tyrosine, from the L series, for use in patients with liver or kidney disease, as well as in patients with nitrogen loss and protein malnutrition. The essential amino acids are selected from valine, leucine, isoleucine, methionine, lysine, phenylalanine, threonine, tryptophan and histidinal, all of the L series. Walser's U.S. Pat. No. 4,320,146-A consists of a mixture of ornithine and arginine salts, with alpha keto analogs of valine, leucine and isoleucine. The compounds are useful, whether alone, singly or in combination, for the treatment of patients with liver disease or kidney disease. In addition, Walser describes in his Patent CA-2317038-C that the administration of a dietary supplement tablet containing a mixture of L-histidine, L-isoleucine, L-leucine, L-lysine, L-methionine, L-phenylalanine, L-threonine, L-tryptophan, L-tyrosine and L-valine, can prevent and/or correct hypoalbuminemia in patients on dialysis. U.S. Pat. No. 4,957,938-A of Anderson et al. describes an improved nutritional formulation for the treatment of patients with renal disease consisting of a mixture of 4 salts of ketoacids of amino acids and L amino acids in which the palatability of the mixture, its thermal stability and shelf life is substantially improved. U.S. Pat. No. 4,752,619-A of Walser et al. also consists of a mixture of salts of L amino acids and of keto-analogues of amino acids. Calton's Patent US-20070141121-A1 describes the use of the soyasaponin fraction alone or in combination with essential amino acids and/or the combination of keto analogs of said essential amino acids. The previous treatment combined with a low-protein diet of the order of 0.6 to 0.8 grams per kilo of weight per day is suggested for the treatment of renal disease secondary to polycystic kidneys.

On the other hand, Patent CA-2331854-C of Lowry et al. describes a liquid nutritional product for oral intake or by feeding tube to improve glomerular function in people with renal failure, which as a main constituent, in addition to proteins, carbohydrates, fats, vitamins and minerals, contains L-arginine, and in which, to improve its palatability and to adjust the pH of the mixture in a range between 6 and 8, lactic acid, adipic acid or malic acid. In another modality of the nutritional product of said patent, the mixture of L-arginine, proteins, carbohydrates, fats, vitamins and minerals includes citric acid in combination with citrates, these being one or more of sodium, potassium and calcium. Although this patent states that L-arginine is essential for improving glomerular function, it is also true that 1) L-arginine is a non-essential amino acid that the organism autogenerates in the urea cycle or Krebs-Henseleit, where it releases a urea molecule and regenerates ornithine, 2) L-arginine is found in the average proteins of our diet by 4.7% (see Table 1), with an atomic mass of 168 and providing 2.632 grams of nitrogen out of the 18.8 grams of nitrogen contained in one mole of average protein; this is in natural conditions, but if these standard proteins are supplemented with a high content of L-arginine, said amino acid carrying 4 nitrogens per molecule, will contribute to increase the metabolic pool of urea, already elevated and unable to be eliminated in a patient with renal failure. Nath's U.S. Pat. No. 5,210,098-A describes the use of pyruvate or its salts intravenously for the prevention or treatment of acute renal failure in patients at risk of having or having had such condition. Patent CN-1285340-C describes the preparation and application of amino acid salts with sulfated polysaccharides in patients with chronic nephritis and renal failure. On the other hand, U.S. Pat. No. 4,677,121-A of Walser et al. proposes the daily administration of alpha ketoisocaproic acid (ketoleucine) doses or an appropriate salt of such acid for the reduction or inhibition of muscle protein degradation in mammals, particularly humans, conditions that usually occur after the recovery of surgeries or diseases involving muscle wasting. Thomas Knerr's U.S. Pat. No. 5,945,129-A describes a process for the production of sterile solutions to be used as dialysis solutions, such as peritoneal dialysis or as an infusion solution containing bicarbonate ions. It describes the steps in the process where esters of carboxylic acids (molecular bonding of an acid with an alcohol) are mixed with bicarbonate salts in aqueous solution and in the presence of sterilization heat. The alcohols may be monovalent or polyvalent and more specifically: ethanol, propranol, isopropanol, glycerol or lactone. In addition, the esters of carboxylic acids are selected from the group consisting of: glucono-o-lactone, diethylsuccinate, diethyltartrate, diethylcitrate, ettilactate and diethylcarbonate. Shin-Jen Shiao's Patent CN-101076325A describes the use of a pharmaceutical composition for reducing serum pH where such a composition contains edible carboxylic acids in a proportion of 0.05 to 99.9 percent of weight. Such acids to which the patent refers are: fumaric, succinic, alpha hydroxyl acids, malic, tartaric, citric, lactic acid, and their corresponding sodium and potassium salts. Additionally, such composition contains caffeine in a proportion of 0.1 to 6 percent of the weight, 0 to 80 percent of the weight of at least one herbaceous and 0 to 96 percent of the total weight of such carrier composition. This pharmaceutical composition is used to prevent, treat or improve the following conditions or entities: allergic diseases, pain, infection, cold, thrombus or clotting during transfusion or dialysis, inflammation, cancer, viral infection, poisoning, memory impairment, caffeine addiction and side effects of the cancer drug paclitaxel. In addition, carboxylic acids can be used in a proportion of 0.05 to 5 percent of weight in combination with animal feed, this being in the proportion of 85 to 99.9 percent of the dry weight. Jin Kyu Park's Patent WO-2007094600-A1 describes a composition for improving memory and learning functions. Such composition contains one or more carboxylic acids selected from the group of: succinic acid, succinic acid salt, fumaric acid, fumaric acid salt, an emulsifier and prune concentrate (plum or maesil) or alcohol extract from maesil.

So far we have seen that patents: Howe's U.S. Pat. No. 2,457,820-A and U.S. Pat. No. 3,764,703-A describe the use of essential amino acid mixtures either orally or intravenously. U.S. Pat. No. 4,100,161-A, U.S. Pat. No. 4,100,293-A, U.S. Pat. No. 4,228,099-A, U.S. Pat. No. 4,296,127-A, U.S. Pat. No. 4,320,146-A, U.S. Pat. No. 4,957,938-A, CA-2317038-C y la U.S. Pat. No. 4,752,619-A, consist of mixed or individual salts of alpha keto analogs of branched chain amino acids, namely valine, leucine and isoleucine, in combinations with L amino acids. On the other hand, Patent US-20070141121-A1 combines the alpha keto analogues of amino acids with the soyasaponin fraction. Patent CA-2331854-C describes the use of a nutritional product based on proteins, lipids and carbohydrates supplemented with L-arginine to be used orally or by feeding tube. Another patent, U.S. Pat. No. 5,210,098-A, consists in using pyruvic acid or its salts for the treatment of acute renal failure. Chinese Patent CN-1285340-C describes the use of salts of sulfated polysaccharides with certain L-amino acids as treatment for patients with chronic renal failure. European Patent EP-0624374-B1 describes the use of sulodexide and medicines containing it in the treatment of patients with diabetic nephropathy. U.S. Pat. No. 5,945,129-A describes the use of parenteral or infusional dialytic solutions consisting of esters of carboxylic acids and bicarbonate. Patent CN-101076325A describes the use of various carboxylic acids combined with caffeine to treat, prevent and ameliorate various conditions. Finally, Patent WO-2007094600-A1 includes succinic acid, fumaric acid or their salts to improve memory and learning.

So far there are records of patents for the treatment of patients with chronic kidney disease and other conditions based on 1) mixtures of amino acids essential for the treatment of patients with chronic terminal or predialytic renal disease, 2) mixtures of alpha keto analogues of essential amino acids in combination with essential L-amino acids, 3) alpha keto analogs mixture with soyasaponin fraction, 4) mixture of sulfated polysaccharides with certain L amino acids, 5) use of sulodexide in diabetic nephropathy and 6) use of pyruvic acid or its salts for the treatment of acute renal failure.

IV. BRIEF DESCRIPTION OF THE FIGURES

FIG. 1 provides a diagram showing a citric acid cycle according to an embodiment.

FIG. 2 provides a diagram showing anaplerotic pathways for replacement of Krebs cycle intermediates according to an embodiment.

FIG. 3 provides a diagram showing external replacement of intermediates of the citric acid cycle according to an embodiment.

V. DESCRIPTION OF THE INVENTION

Our novel patent consists of a mixture of dicarboxylic and tricarboxylic acids for the nutritional treatment of patients with chronic renal failure and other conditions, such as acute renal failure, acute or chronic hepatopathy with hyperammonemia, congenital diseases with enzymatic alterations of the urea cycle, pathological human conditions with negative nitrogen balance, namely: sepsis, burns, postoperative, parenteral nutrition supplement entailing mixing of amino acids, enteral feeding complement, sarcopenia, cancer, malnutrition, and diabetes mellitus. More specifically, said mixture consists of 1) racemic mixture of malic acid (hydroxybutanedioic acid), 2) fumaric acid (trans-butenedioic acid), 3) succinic acid (butanedioic acid) and 4) citric acid (2-hydroxypropane-1,2,3-tricarboxylic acid). Such acids may be used individually or in the following combinations, namely:

1.—citric acid in combination with succinic acid, fumaric acid and malic acid (a mixture of four acids)
2.—succinic acid in combination with fumaric acid and malic acid (mixture of three acids)
3.—succinic acid in combination with citric acid and malic acid (mixture of three acids)
4.—citric acid in combination with fumaric acid and malic acid (mixture of three acids)
5.—citric acid in combination with fumaric acid and succinic acid (mixture of three acids)
6.—fumaric acid in combination with malic acid (mixture of two acids)
7.—succinic acid in combination with malic acid (mixture of two acids)
8.—succinic acid in combination with fumaric acid (mixture of two acids)
9.—citric acid in combination with malic acid (mixture of two acids)
10.—citric acid in combination with fumaric acid (mixture of two acids)
11.—citric acid in combination with succinic acid (mixture of two acids)
12—citric acid alone (a single acid, not mixed with succinic, fumaric or malic acid)
13.—succinic acid alone (a single acid, not mixed with citric, fumaric or malic acid)
14.—fumaric acid alone (a single acid, not mixed with citric, succinic, or malic acid)
15.—malic acid alone (a single acid, not mixed with citric, succinic, or fumaric acid)

Of such combinations, the number one is the most complete because it consists of the mixture of three dicarboxylic acids, namely, succinic acid, fumaric acid, malic acid and a tricarboxylic acid, citric acid; in total four different acids. However, said mixture of four acids is neither exclusive nor limiting, since the other combinations of three carboxylic acids, namely, of combination 2 to combination 5, as well as combinations of mixtures of two carboxylic acids selected from citric acid, malic acid, fumaric acid and succinic acid, namely, combinations 6 to 11, are also beneficial in the nutritional treatment of chronic renal failure in stages 3, 4 and 5 and other conditions. Finally, the use of any of the aforementioned acids: citric acid, malic acid, fumaric acid or succinic acid alone, not in combination with each other, items 12 to 15, are also beneficial in the treatment of chronic renal failure, as well as in other pathologies referred to in the field of use of the present invention, such as the illustrative case of Nath's U.S. Pat. No. 5,210,098-A, wherein pyruvic acid or its salts are used for the treatment of acute renal failure.

The scientific bases of our novel invention, contrary to what has been said, stated and discussed in previous patent claims where, certainly and effectively, the administration of alpha keto analogs of branched chain amino acids, either alone or in combination with L-amino acids, promote the formation of their corresponding amino acids: valine, leucine and isoleucine, by obtaining via transamination an amino group, our bases are at the level of the citric acid cycle where the reversible transamination of oxalacetate occurs to generate aspartate or by anaplerotic reaction of replacement, aspartate deamination, to generate oxalacetate. In addition to this reaction, another one occurring at the citric acid cycle level involves the reversible transamination of alpha keto glutarate to generate glutamate or, inversely, glutamate deamination to generate alpha keto glutarate. I repeat, our scientific bases are supported by a detailed study of:

1.—Tricarboxylic acid cycle where it is seen that the entry to the cycle is via the acetyl coenzyme A (see FIG. 1), which, together with oxaloacetate, regenerates citric acid, the first target of our invention. After some intermediate steps the citrate generates alpha-ketoglutarate, which subsequently generates succinyl coenzyme-A, which in turn generates succinate, the second target of our invention. Succinate loses two electrons by oxidation and creates fumarate, third objective of our invention. In the immediate metabolic step, the fumarate is hydrated to form malate, the fourth objective of our invention. It should be noted that the salts, among others, citrate, succinate, fumarate and malate are mentioned in the tricarboxylic acid cycle. Our invention consists of mixtures of citric, succinic, fumaric and malic acids, which in the aqueous environment of the organism dissociate into their corresponding citrate, succinate, fumarate and malate ions. Of special interest is that the cycle of citric acid is a universal cycle that takes place not only in the human being, but in the three domains of life on earth, i.e., in 1) domain eukarya where animalia, plantae, fungi and protista kingdoms are included, 2) domain archaea and 3) domain bacteria. This cycle is a universal cycle and constitutes the center or axis of the general metabolism of any cell, be it eukaryote with true nucleus, as is the case with all the cells of the human being, or prokaryotic cell, as is the case with bacteria that do not possess true nucleus. Said citric acid cycle is an amphibole cycle involving two very important general functions or pathways that are interrelated, namely:

1.a) Function or catabolic pathway, in which nutrients such as proteins via amino acids, carbohydrates via glucose, triacylglycerols via glycerol and fatty acids, end up as pyruvate before entering the cycle of tricarboxylic acid. By losing a carbon and generating $CO_2$, pyruvate is converted to acetyl coenzyme A and when it binds with the oxalacetate it regenerates the citrate to enter the citric acid cycle through the catabolic pathway, generating energy through the formation of ATP and various electron carriers like NAD and FAD.

1.b) Function or anabolic pathway, in which certain intermediates of the citric acid cycle are used for the biosynthesis of monomeric molecules. Thus, for glucose biosynthesis (gluconeogenesis), oxalacetate is used, and for biosynthesis of fatty acids we use acetyl coenzyme A. For the biosynthesis of non-essential amino acids (glycine, L alanine, L asparagine, L aspartate, L cysteine, L glutamate, L glutamine, L proline, L serine and L tyrosine) the oxalacetate intermediate is used as the initiator of synthesis, which will be formed through the acids of our invention: succinic acid, fumaric acid and malic acid, which in the aqueous medium of our body form the corresponding succinate, fumarate and malate. Thus succinate, by the action of the enzyme succinate dehydrogenase, generates fumarate. In turn, fumarate, by action of the enzyme fumarase, generates L malate. Finally, L malate, by the action of the enzyme malate dehydrogenase, produces oxaloacetate. Another cycle intermediate is alpha-ketoglutarate which serves as the initiator to form glutamic acid by reversible transamination. Then, by additional transamination, form glutamine, as well as other related amino acids. Said alpha ketoglutarate is generated by metabolic reactions exerted on the citric acid, which in the aqueous environment of the organism is dissociated in citrate, which is part of our invention. These methabolic reactions involve the action of the enzyme aconitase on the citrate to generate cis-aconitate. In a second reaction, the same enzyme aconitase acts on the cis-aconitate to form isocitrate. In the next metabolic step, the enzyme isocitrate dehydrogenase acts on the isocitrate to generate alpha ketoglutarate.

As shown in FIG. 2, these amino acid biosynthetic pathways, glucose and fatty acids, are pathways that extract intermediates from the cycle and are known as cataplerotic pathways or reactions, which hypothetically speaking, when extracting intermediates from the cycle would exhaust it. This is not the case because, in return for this cataplerotic pathway, and since the citric acid cycle cannot be interrupted, there are replacement pathways or reactions of these intermediaries known as anaplerotic pathways or reactions, of which the most important is the catabolized by the enzyme pyruvate carboxylase that generates oxalacetate from pyruvate (reaction 1). Another anaplerotic reaction for the replacement of cycle intermediates involves the direct conversion of phosphoenolpyruvate by the action of the enzyme phosphoenolpyruvate carboxylase to oxalacetate (reaction 2). Another involves reversible transamination from aspartate to oxalacetate (reaction 3). Furthermore, by the action of the malic enzyme or malate dehydrogenase on pyruvate, it catalyzes the reductive carboxylation thereof to generate malate (reaction 4). Finally, glutamate generates alpha ketoglutarate by reversible transamination (reaction 5). To sum up, so far 3 anaplerotic reactions generate and replenish oxaloacetate, namely, anaplerotic reaction from phosphoenolpyruvate to oxalacetate, anaplerotic reaction from pyruvate to oxalacetate and anaplerotic reaction from aspartate to oxaloacetate. A fourth anaplerotic reaction generates malate from pyruvate, and a last and fifth anaplerotic reaction generates alpha ketoglutarate from glutamate.

In conclusion, the citric acid cycle is:

a) A universal metabolic cycle that takes place in all living beings and includes the three domains: eukaria, which in turn includes animalia and the human being—purpose of our invention—plantae, fungi, protist, and other two domains, the domain archaea and the domain bacteria.

b) A metabolic cycle that is situated at the axis of the general metabolism.

c) An amphibole cycle with two interrelated pathways, a catabolic pathway involving the use of carbon compounds to generate energy via ATP, as well as electron carriers such as NAD and FAD; and an anabolic pathway in which cycle intermediates, more specifically oxalacetate and alpha ketoglutarate, are used as initiator compounds for building other molecules, most notably non-essential amino acids—subject and consideration of the scientific basis of our patent.

d) In turn, the anabolic pathway, which involves subtracting certain intermediates (oxalacetate, alpha-ketoglutarate and acetyl coenzyme A) to form new molecules different from the compounds of the cycle, known as cataplerotic reactions, is compensated by reactions of replenishment or filling of intermediates, called anaplerotic reactions.

2.—Another scientific basis of our invention involves the knowledge that in the urea cycle arginine is used to generate urea and ornithine by the action of arginase. This cycle is energy-dependent, consuming ATP in the formation of urea.

Urea, the main product of excretion of nitrogen compounds in ureotelic animals, as is the case of humans, is a small molecule with a molecular weight of 48, which by the action of intestinal urease is split into carbon dioxide and ammonium.

Non-ureotelic animals, such as fish, remove their nitrogenous waste products to the aquatic environment in the form of ammonium, not requiring conversion to urea.

Animals such as the bear in the wintering period do not form urine, so there must be alternate metabolic pathways to reuse the formed urea.

The Dalmatian dog, being ureotelic, eliminates its nitrogenous wastes via uric acid.

Reptiles and birds eliminate their nitrogenous waste via uric acid formation.

In the insects there are Malpighian tubules, which consist of tubular structures in which the blind end of the tube is in contact with the hemolymph and the other end leads into the final part of the insect's intestine.

From the anatomical point of view, in flat worms or plathelminthes the first structures specialized in excretion are given: protonephridia that on the one hand connect with the coelom and on the other they open to the outside of the animal through the nephridiopores. An even more advantageous structure in the evolution are the metanephridia appearing in mollusks and annelids. This consists of an open tubele in which the inner end opens into the coelom and the outer end is opened to the outside by means of a nephridiopore.

With the above we notice a metabolic diversity regarding the elimination of nitrogenous waste products: ammonium in fish, uric acid in reptiles and birds, and urea in ureothelial animals. There is also an anatomical diversity that remotely targets the relationship between the urinary system, the digestive system and the skin. By this we refer to the Malpighian tubules that connect to the intestine of insects, which explains the transfer of a certain amount of urea to the intestine, about 25% of the serum urea, as well as the elimination of approximately 10% of serum urea through sweat, perhaps a reminder of the time when life on Earth was at the stage of mollusks and annelids.

Our invention consists or implies (see FIG. 3): first objective, the replacement of citrate from citric acid which, in subsequent metabolic steps, will first generate cis aconitate, then isocitrate and finally alpha keto glutarate; second objective, replacement of succinate from succinic acid, which in subsequent steps will generate fumarate, then malate, and then oxaloacetate; third objective of our invention, replacement of fumarate through fumaric acid which in a subsequent step will generate malate, and this, in turn, will generate oxaloacetate; fourth objective, replacement of malate through malic acid, which in the subsequent step will generate oxaloacetate. Thus, in comparing the five anaplerotic reactions of the citric acid cycle, two of them, for our interest, are not considered since they involve transamination from aspartate to oxalacetate and transamination from glutamate to alfacetoglutarate, since they lead to deamination of existing amino acids. Then, there are three intermediate replacement routes left that do not involve transamination. Two of them replenish oxalacetate via pyruvate and phosphoenolpyruvate, and one of them replaces malate via pyruvate.

Our invention, unlike prior patents based on the administration of essential amino acids orally or intravenously, or the use of alpha keto analogs of essential branched-chain amino acids in combination with essential amino acids, as well as unlike what happens in vivo inside the cell, and more specifically at the mitochondrial level—because the citric acid cycle is performed at the mitochondrial level—our first objective involves the replacement of citrate through citric acid, which in subsequent reactions results in the formation of carbon dioxide and alpha keto glutarate, in molar proportions; thus, one mole of citrate generates one mole of carbon dioxide and one mole of alpha keto glutarate. This does not occur in nature because under biological conditions citrate is regenerated by the reaction of acetyl Coenzyme A, catalyzed by the enzyme citrate synthase on the oxaloacetate to generate citrate. Second objective, replacement of succinate through succinic acid, which will give fumarate, then malate and finally oxalacetate, replacement condition of our invention that does not occur in biological systems either. Third objective, consisting of the replacement of fumarate through fumaric acid that will give malate and finally oxalacetate, replacement of our invention which, like the replacement of succinate, does not occur in biological systems. Fourth objective, consisting of the replacement of malate through malic acid, which in the case of biological systems is carried out by action on the pyruvate of the malic enzyme to generate malate, but in the case of our invention, a direct replacement is provided without intervening or acting on any substrate or by the action of specific enzyme.

In addition, our invention consists in the option of adding other dicarboxylic acids such as tartaric acid and/or cream of tartar to the mixture to improve the palatability and solubility of said mixture, and additionally phosphorus chelating agents such as calcium carbonate and/or calcium acetate and/or calcium gluconate and/or calcium lactate, which are extremely beneficial in the treatment of patients with chronic renal failure in stages 4 and 5, because in this condition hyperphosphataemia is extremely common, especially in patients with chronic long-term renal failure.

An additional element of the present patent is the incorporation of sodium bicarbonate into the mixture of dicarboxylic acids (succinic acid, fumaric acid, malic acid and tricarboxylic citric acid). Sodium bicarbonate is beneficial in patients with renal failure, as these occur with chronic metabolic acidosis. In addition, it serves to balance the pH of the mixture or the carboxylic acids used in a unique way and as an antacid effect.

Another optional element or elements (may be present or not) additional to the mixtures of this patent, is the addition of food additives to improve patient adherence to medical treatment: (1) Artificial sweeteners such as aspartame, acesulfame and/or sucralose, and (2) natural sweeteners such as disaccharides: sucrose and/or lactose, or monosaccharides: glucose and/or fructose.

In addition, optional additional nutraceutical substances (which may or may not be present) are incorporated into the mixtures of this invention, such as: inulin, maguey honey, taurine, msm (methylsulfonylmethane), alpha lipoic acid and L carnitine.

As part of the oral treatment of the patient with chronic renal failure, in addition to the specific medications for each patient, supplements consisting of ascorbic acid, folic acid, ferrous sulfate, calcitriol and complex b are routinely prescribed, so that in order to reduce to the maximum and as much as possible the number and diversity of the different and various medicines referred to, the latter, ascorbic acid, folic acid, ferrous sulfate, calcitriol and b complex, are optionally incorporated into the carboxylic acid mixture, a possible condition given the high solubility of these as well as their pleasant palatability.

In order to calculate the amount of dicarboxylic acids to be used which are sufficient to finally generate oxalacetate and alpha keto glutarate, and to capture ammonium via transamination derived from the metabolism of amino acids, and on a much smaller scale of the metabolism of the pyrimidine bases and other compounds carrying amino, amido or imino groups, we will resort to the following data:
1.—A restricted diet of 0.6 to 0.8 grams per kilo of patient weight per day is suggested; then in a man of 70 kilos, the amount of protein to be consumed will be 42 to 56 grams per day, ideally high quality biological proteins.
2.—The average amino acids for a large number of proteins—the same ones to be ingested—is as follows: see Table 1—column 4. Of these twenty amino acids, 14 have a nitrogen (N), 4 of them carry 2 nitrogens, 1 of them 3 nitrogens and 1 of them 4 nitrogens. Their atomic weights are expressed in column 6. Correlating the above data we have that one mole of average proteins would weigh 125.76 grams and would contain 18.802 grams of nitrogen.

TABLE 1

Average composition of the amino acids constituent of the average proteins.

| NAME OF A.A. | EMPIRICAL FORMULA | PRESENCE IN PROTEINS[0] | N ATOMS PER A.A. | ATOMIC MASS[1] | PROPORTIONAL MASS[2] | N ATOMS[3] | N ATOMS[4] |
|---|---|---|---|---|---|---|---|
| ALANINE | O2C3H8N1 | 9% | 1 | 90 | 8.1 | 0.09 | 1.26 |
| ARGININE | O2C6H16N4 | 4.7% | 4 | 168 | 7.896 | 0.188 | 2.632 |
| ASPARAGINE | O2C4H9N2 | 4.4% | 2 | 117 | 5.148 | 0.088 | 1.232 |
| ASPARTIC ACID | O2C4H8N1 | 5.5% | 1 | 102 | 5.61 | 0.055 | 0.77 |
| CYSTEINE | O2C3H8S1N1 | 2.8% | 1 | 122 | 3.416 | 0.028 | 0.392 |
| GLUTAMINE | O3C5H11N2 | 3.9% | 2 | 147 | 5.733 | 0.078 | 1.092 |
| GLUTAMIC ACID0 | O4C5H10N1 | 6.2% | 1 | 148 | 9.176 | 0.062 | 0.868 |
| GLYCINE | O2C2H6N1 | 7.5% | 1 | 76 | 5.7 | 0.075 | 1.05 |
| HISTIDINE | O2C6H12N3 | 2.1% | 3 | 158 | 3.318 | 0.063 | 0.882 |
| ISOLEUCINE | O2C6H14N1 | 4.6% | 1 | 132 | 6.072 | 0.046 | 0.644 |
| LEUCINE | O2C6H14N1 | 7.5% | 1 | 132 | 9.9 | 0.075 | 1.05 |
| LYSINE | O2C6H16N2 | 7% | 2 | 148 | 10.36 | 0.14 | 1.96 |
| METHIONINE | O2C5H12S1N1 | 1.7% | 1 | 150 | 2.55 | 0.017 | 0.238 |
| PHENYLALANINE | O2C9H13N1 | 3.5% | 1 | 167 | 5.845 | 0.035 | 0.49 |
| PROLINE | O2C5H10N1 | 4.6% | 1 | 116 | 5.336 | 0.046 | 0.644 |
| SERINE | O3C3H8N1 | 7.1% | 1 | 106 | 7.526 | 0.071 | 0.994 |

TABLE 1-continued

Average composition of the amino acids constituent of the average proteins.

| NAME OF A.A. | EMPIRICAL FORMULA | PRESENCE IN PROTEINS[0] | N ATOMS PER A.A. | ATOMIC MASS[1] | PROPORTIONAL MASS[2] | N ATOMS[3] | N ATOMS[4] |
|---|---|---|---|---|---|---|---|
| THREONINE | O3C4H10N1 | 6% | 1 | 120 | 7.2 | 0.06 | 0.84 |
| TRYPTOPHAN | O2C11H16N2 | 1.1% | 2 | 208 | 2.288 | 0.022 | 0.308 |
| TYROSINE | O3C9H14N1 | 3.5% | 1 | 184 | 6.44 | 0.035 | 0.49 |
| VALINE | O2C5H12N1 | 6.9% | 1 | 118 | 8.142 | 0.069 | 0.966 |
|  |  | 100% |  |  | 125.76 | 1.34 | 18.8 |

[0]Average for a large number of proteins. Individual proteins may exhibit significant variations with respect to these values.
[1]The atomic masses of the elements constituting amino acids are: Hydrogen 1, Carbon 12, Nitrogen 14, Oxygen 16 and Sulfur 32.
[2]The proportional mass of each amino acid (A.A.) was obtained by multiplying the percentage of each A.A. found in an average protein by its atomic mass. Hence, by adding up the proportional mass of each amino acid that makes up a protein, we obtain that the weight of an average protein is 125.76 grams.
[3]The nitrogen atoms of each amino acid in proportion to their appearance in proteins are equivalent to their mass proportional by the number of atoms per amino acid among its atomic mass. The sum of the nitrogen atoms of each A.A. found in an average protein is equal to 1.34.
[4]Since one mole of nitrogen weighs 14 grams, it can be deduced that 1.34 moles of nitrogen equals 18.8 grams.

According to a diet restricted to 0.6 grams of protein per kilo of weight per day, a person of 70 kilos of weight would ingest 42 grams of protein, which would provide 6.28 grams of nitrogen (equivalent to 448.54 millimoles of nitrogen).

In the case of a diet of 0.8 grams of protein per kilo of weight per day, a person of 70 kilos of weight would ingest 56 grams of protein, which would provide 8.37 grams of nitrogen (equivalent to 598.05 millimoles of nitrogen).

Taking into account the Avogadro's number, where one mole of any substance is equal to $6.022 \times 10^{23}$ molecules per mole (gram molecule), we can conclude that:

3.—To capture 6.28 grams of nitrogen (448.54 millimoles of nitrogen, as one mole of nitrogen equals 14 grams) contained in 42 grams of protein, we need the same amount of millimoles of dicarboxylic and tricarboxylic acids; this in basal conditions, it is obvious to mention that in situations of stress, such as sepsis, surgery, burns, consumptive diseases and diabetes, the requirements would increase.

Since the carboxylic acid mixture has an average mass of 140 to equal parts (see Table 2), one mole of this mixture is equal to 140 grams. To obtain 448.54 millimoles of such acids, 62.79 grams of these are needed, and to obtain 598.05 millimoles 83.73 grams of dicarboxylic and tricarboxylic acids are needed.

TABLE 2

Average molar weight of carboxylic acids and their mixtures in equal parts.

| CARBOXYLIC ACIDS | ATOMIC MASS |
|---|---|
| Succinic Acid | 118 |
| Fumaric Acid | 116 |
| Malic Acid | 134 |
| Citric Acid | 192 |
| AVERAGE WEIGHT (in equal proportions) | 140 |

Excretion of urea and other low molecular weight nitrogen compounds is carried out through sweat in 10%, feces in 25%, as ammonium through the urine in 10% and another 10% by residual renal function. This represents about 35% of the removal of nitrogen and nitrogen compounds alternately to renal excretion and 20% renally (10% in ammonium form as such, and 10% as residual renal function). If one takes into account that of the daily intake of proteins about 55% of the nitrogens contained in them are eliminated through these pathways, the need for ingestion of the carboxylic acids can be reduced by half approximately. This would maintain the daily requirement thereof in the order of 31.40 grams to 41.86 grams of carboxylic acids for an intake of 42 and 56 grams of protein respectively.

The effects and, consequently, the benefits of this invention are:

1.—Capture of ammonium before the formation of urea at the liver level, thereby
 1.1—reducing the concentration of ammonium in the body and the toxic effects thereof and
 1.2—reducing the concentration of urea in the organism and its toxic effects thereof.
2.—Capture of ammonium via dicarboxylic acids: succinic acid, fumaric acid and malic acid, which by enzymatic reactions thereon end up in the ketoacid oxalacetate, which, by transamination, forms aspartate and other related amino acids. In turn, citric acid, after passing to cis-aconitate and isocitrate, loses a carbon generating $CO_2$ and alpha-ketoglutarate, which by transamination will generate glutamate and related amino acids.
 2.1—improvement of nitrogen balance,
 2.2—increase in the synthesis of non-essential amino acids,
 2.3—improvement of nutritional status and
 2.4—increase in serum albunim levels in the blood.
3.—Improvement of palatability versus prior patents based on mixtures of calcium salts of alpha keto analogs of branched chain amino acids and mixture of L amino acids.
4.—Improvement of patient adherence to treatment.
5.—Improvement of the quality of life.
6.—Decrease in treatment costs.
7.—Additionally the phosphate is chelated from food by incorporating calcium carbonate and/or calcium acetate and/or calcium gluconate and/or calcium lactate into the mixture. This incorporation of calcium salts into the mixture contains the following benefits:
 7.1—Contributes to the mixture pH damping,
 7.2—gastric protection,
 7.3—additional cost reduction and overall adherence to the treatment of end-stage renal disease, due to the additional use of phosphorus-chelating drugs, otherwise the patient should consume phosphorus-chelating drugs separately.
8.—Improvement of metabolic acidosis, a very common condition of patients with renal failure stages 4 and 5, with the addition of sodium bicarbonate which is added for two purposes:
 8.1—dampening of the dicarboxylic acids mixture,
 8.2—improvement of metabolic acidosis characteristic of CRF stages 4 and 5, and 8.3—protection against hyperkalemia and the adverse and potentially lethal effects thereof, which is aggravated in the presence of acidosis.

The treatment with dicarboxylic and tricarboxylic acids prevents, preserves and even improves renal function, avoiding renal replacement therapy, poor quality of life of the patient and the extremely high financial costs borne by relatives and/or institutions of the health sector of the States. Finally, it prevents frequent hospitalizations as a consequence of the inherent therapeutic procedures and the complications thereof. In other patients it delays deterioration of renal function and the urgent need for renal replacement therapy. In this group of patients, laboratory parameters and quality of life are maintained favorably while waiting for a kidney transplant. In others, it is used as a treatment complementary to renal replacement therapy to improve the patient's quality of life and improve laboratory parameters.

The following clinical cases illustrate the benefits and achievements of this invention:

Case 1.—Retrospective study: A 82-year-old male with a history of Diabetes Mellitus type II of over 25 years of evolution was diagnosed with Terminal Renal Failure Stage V in August 2010 with a serum urea of 129.5, creatinine 3.3, BUN 60.51, hb 11.8, potassium 5.1, phosphorus 4.5, calcium 9.4 and general urine with proteinuria of 250 mg/liter. Nephrology started protocol for initiation of peritoneal dialysis. In November 2010, before starting treatment with oral carboxylic acids, the 24-hour urine creatinine clearance was 16.46 ml/min, with a urinary volume of 17.5 deciliters, serum creatinine of 3.14 and urinary creatinine of 39.82 mg/dl. The patient refused peritoneal dialysis renal replacement therapy and initiated treatment consisting of the current invention, combined with a low protein diet of the order of 0.6 to 0.8 grams of protein per kilo per day. In July 2014, he broke is hip, which resulted in a total prosthesis thereof, blood transfusion of 2 units and his biochemical parameters were: hb 11.5, urea 141, creatinine 3.2, BUN 66, serum ammonium 5 (normal 9-33). In August 2014 his 24-hour urine creatinine clearance was 25.36 ml/min with a urinary volume of 23.7 deciliters, serum creatinine of 2.41 and urinary creatinine of 33.91. In November 2014, the patient completed 4 years in treatment. An improvement in creatinine clearance in the 24-hour urine of an initial pretreatment value of 16.46 ml/min is observed, which even 4 years later remains above these values, the last clearance being 25.36 ml/min.

Case 2.—Retrospective study: a 50-year-old female with a history of severe arterial hypertension with a previous figure of 240/140 mmHg. In September 2013 she started renal replacement therapy with hemodialysis, 3 sessions per week for 2 consecutive months. After 2 months of hemodialysis, the laboratory parameters are: hb 10, serum creatinine 6.7, urea 133, 24-hour urine creatinine clearance 10.84 ml/min. In November 2013, she started treatment with oral carboxylic acids, as well as a low-protein diet of 0.6 to 0.8 grams/kilo/day. She did not continue attending the hemodialysis sessions, so at the end of January 2014 the central catheter was removed. The last assessment of the patient was in September 2014. It is should be mentioned that during the last two months the patient had suspended treatment with carboxylic acids because they did not have them. Her laboratory tests in September 2014 are: hb 9.6, serum creatinine 5.1, urea 200, BUN 84, potassium 5.2, phosphorus 6.8, calcium 8.2, albumin 4.4. After 60 days of hemodialysis, one year without dialytic treatment and 2 months of discontinuation of carboxylic acid treatment, the patient showed a decrease of 0.4 in hemoglobin, reduction in serum creatinine from 6.7 to 5.1, and a moderate increase in urea from 133 to 200.

Case 3.—Retrospective Study: A 72-year-old male with a history of systemic arterial hypertension, diabetes mellitus of 40 years of evolution and ESRD. In November 2012 the laboratory analysis showed: hb 12.2, serum creatinine 5.3, urea 127, BUN 59. He refused renal replacement therapy and in November 2012 he began with treatment of oral carboxylic acids. At this time he had a serum creatinine of 6.74, urea 209, BUN 97.7. In November 2013, the date of his last visit, his laboratory tests were: serum creatinine of 3.9, urea of 58, BUN 27. Eight months later he had pneumonia and myocardial infarction, endotracheal intubation was performed and he died as a consequence of myocardial infarction. In a year of treatment with carboxylic acids, the patient's nitrogen levels were improved: serum creatinine was reduced by more than 42% and urea decreased by 72%.

Case 4—Retrospective study: 35-year-old male diagnosed with end-stage renal disease secondary to hypoplastic kidneys. In May 2014, he started renal replacement therapy with acute dialysis; his laboratory tests at that date were hb of 6.9, serum creatinine 21.3, urea 216 and potassium 4.4. One month later he started with intermittent peritoneal dialysis consisting of 20 sessions each week. At the onset of IPD, his laboratory tests showed hb of 7.4, serum creatinine 17, urea 226, uric acid 10.1, urine creatinine clearance of 24 hours of 2.65 ml/minute. In July 2014, laboratory tests show: hb 8.4, serum creatinine 17.7, urea 215. On September 2 he started treatment with oral carboxylic acids, coupled with a low protein diet. On Sep. 22, 2014, 20 days after initiating such treatment, he began with continuous ambulatory peritoneal dialysis consisting of 4 sessions per day. On Oct. 20, 2014, two months after starting treatment with carboxylic acids and one month after starting ambulatory peritoneal dialysis, he showed dramatic laboratory studies: hb 12.7, serum creatinine 12.77, and urea 86.2.

The invention claimed is:

1. A mixture comprising:
citric acid, succinic acid, fumaric acid and malic acid, in combination with sodium bicarbonate, calcium carbonate and calcium lactate,
wherein the mixture provides, per dose, citric acid from 56 to 600 millimoles (10.8 grams to 116.4 grams), succinic acid from 56 to 600 millimoles (6.6 grams to 70.8 grams), fumaric acid from 56 to 600 millimoles (6.5 grams to 69.6 grams), and malic acid from 56 to 600 millimoles (7.5 grams to 80.4 grams) to reduce uremia in patients with chronic renal failure.

2. The mixture of claim 1, wherein said mixture is in the form of a powder or effervescent tablets.

3. The mixture of claim 2, further comprising vitamin C, folic acid, ferrous sulfate, B complex and/or calcitriol.

4. The mixture of claim 2, further comprising artificial sweeteners of acesulfame, aspartame and/or sucralose.

5. The mixture of claim 2, further comprising fructose and/or glucose; sucrose and/or lactose; and/or oligosaccharides of inulin and/or maguey honey.

6. The mixture of claim 2, further comprising taurine and/or L carnitine.

* * * * *